(12) United States Patent
Kroeckel

(10) Patent No.: US 8,777,937 B2
(45) Date of Patent: Jul. 15, 2014

(54) CATHETER FOR MAGNETIC RESONANCE-SUPPORTING INTERVENTIONAL PROCEDURES

(75) Inventor: Horst Kroeckel, Bamberg (DE)

(73) Assignee: Siemens Aktiengesellschaft, Munich (DE)

( * ) Notice: Subject to any disclaimer, the term of this patent is extended or adjusted under 35 U.S.C. 154(b) by 1715 days.

(21) Appl. No.: 11/782,678

(22) Filed: Jul. 25, 2007

(65) Prior Publication Data
US 2008/0033281 A1 Feb. 7, 2008

(30) Foreign Application Priority Data
Jul. 25, 2006 (DE) .................. 10 2006 034 389

(51) Int. Cl.
*A61B 18/18* (2006.01)
(52) U.S. Cl.
USPC .............. 606/33; 607/154; 607/156
(58) Field of Classification Search
CPC .............................. A61B 2018/1846
USPC ........ 606/32–33; 600/422, 433; 607/154, 156
See application file for complete search history.

(56) References Cited

U.S. PATENT DOCUMENTS

| | | | | |
|---|---|---|---|---|
| 4,559,951 A | * | 12/1985 | Dahl et al. | 600/374 |
| 4,917,104 A | * | 4/1990 | Rebell | 600/585 |
| 5,351,691 A | * | 10/1994 | Brommersma | 600/462 |
| 5,405,346 A | * | 4/1995 | Grundy et al. | 606/41 |
| 5,429,139 A | | 7/1995 | Sauter | |
| 5,489,270 A | * | 2/1996 | van Erp | 604/95.04 |
| 5,500,012 A | * | 3/1996 | Brucker et al. | 607/122 |
| 6,190,382 B1 | * | 2/2001 | Ormsby et al. | 606/33 |
| 6,690,970 B1 | * | 2/2004 | Taheri et al. | 607/9 |
| 6,701,176 B1 | | 3/2004 | Halperin et al. | |
| 2003/0028095 A1 | * | 2/2003 | Tulley et al. | 600/422 |
| 2003/0040787 A1 | * | 2/2003 | Flynn et al. | 607/122 |
| 2003/0114844 A1 | * | 6/2003 | Ormsby et al. | 606/33 |
| 2003/0135110 A1 | | 7/2003 | Leussler | |
| 2004/0039371 A1 | * | 2/2004 | Tockman et al. | 604/528 |
| 2005/0165301 A1 | | 7/2005 | Smith et al. | |
| 2007/0219548 A1 | * | 9/2007 | Carr | 606/33 |
| 2008/0161889 A1 | * | 7/2008 | Paul et al. | 607/102 |

* cited by examiner

*Primary Examiner* — Jaymi Della
(74) *Attorney, Agent, or Firm* — Schiff Hardin LLP

(57) ABSTRACT

A catheter for magnetic resonance-supported interventional procedures has an electric cable that connects a first electric component attached to one catheter end with a second electric component attached to the other catheter end, with the electric cable being coiled at least in sections thereof.

6 Claims, 2 Drawing Sheets

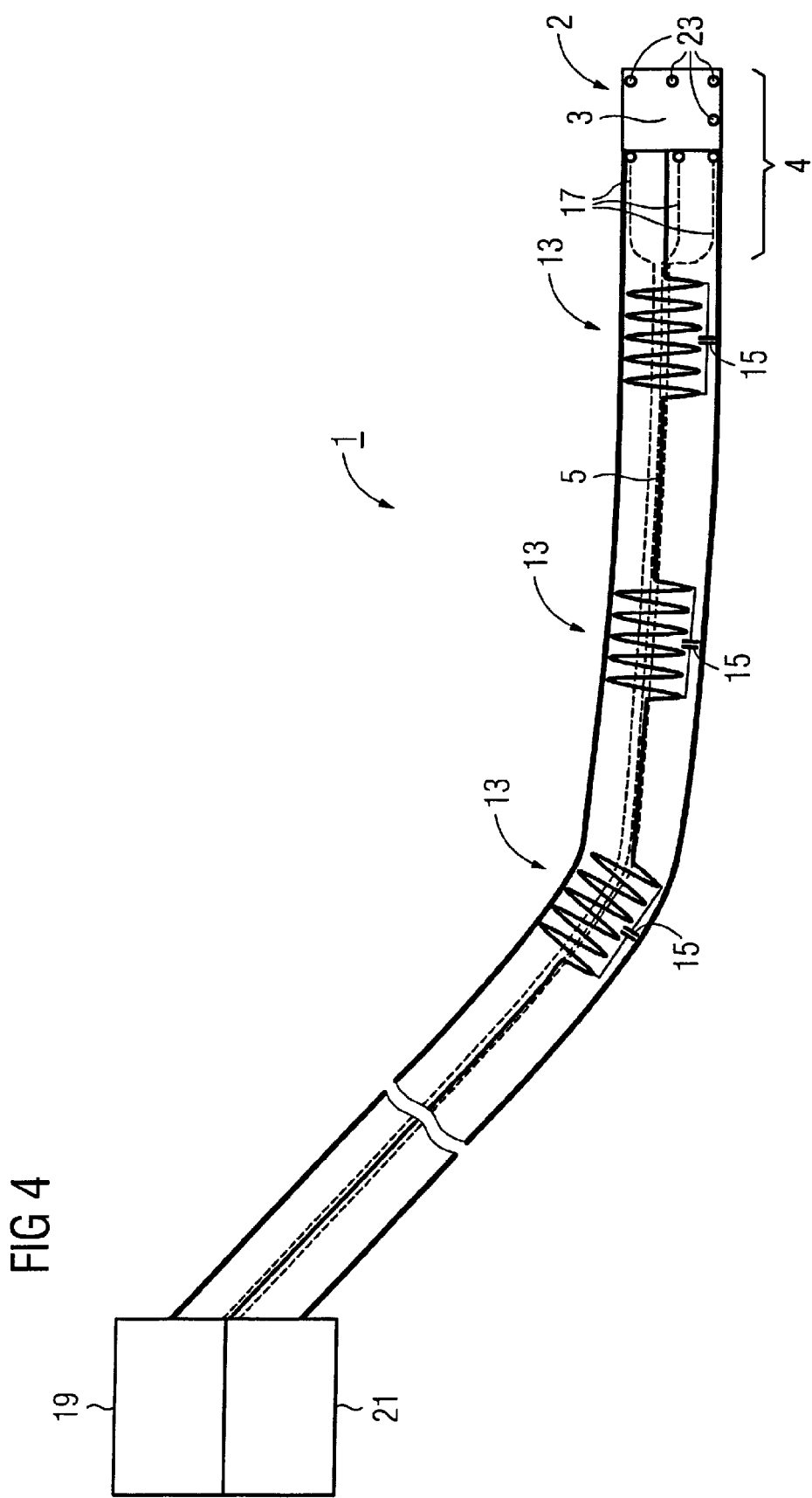

CATHETER FOR MAGNETIC RESONANCE-SUPPORTING INTERVENTIONAL PROCEDURES

BACKGROUND OF THE INVENTION

1. Field of the Invention

The present invention concerns a catheter of the kind used in magnetic-resonant-supported interventional procedures.

2. Description of the Prior Art

In medicine, catheter-supported examination and treatment procedures are established procedures in which usually a long, thin catheter is inserted into a hollow organ of the body.

Catheter-supported procedures are frequently used, for instance, in the vascular system and the heart. For this purpose, a catheter is inserted into well-accessible arm and leg veins or arteries and fed forward to the place to be examined and/or treated. Known examinations performed in the context of intracardiac catheter examinations are, for instance, a representation of hemodynamics by means of injected contrast agents, measurements of the electric activity of the heart in the context of an electrophysiological examination, performance of pressure and/or oxygen measurements in various parts of the circulatory system, a representation of the heart ventricles and coronary vessels balloon dilatation or stenting of constricted vessels, treatment of cardiac defects and ablation of additional stimulation paths or of myocardial tissue.

Depending on the intended use, of the inserted catheter, the catheter tip can have different designs. For ablation of tissue, catheters are known that carry at their tip a probe designed as a high frequency antenna (subsequently also referred to as RF antennas; RF standing for high frequency) by means of which RF energy is discharged into the surrounding tissue in order to coagulate the tissue. Alternatively, probes in the form of ultrasound transducers or laser sources are known by means of which tissue can also be destroyed by means of ultrasound or laser beams. Furthermore, catheters are known that are used for cryoablation (destruction of tissue by means of freezing) or for alcoholic ablation (destruction of tissue by means of injections of alcohol).

Usually, in the process, the catheter is fed forward in the tissue under visual control, which previously has been facilitated by means of X-ray examination. However, in several ways, the use of X-rays is problematic, especially since both the attending physician and the patient are partially exposed to serious radiation levels. In fact, it has been proposed to perform such interventions by remote-control so that at least the attending physician is protected against the X-rays. In this case, a magnetic catheter tip can be navigated by means of an external magnetic field. Even these procedures involve disadvantages. The construction of such a system is comparatively expensive, quick intervention in the event of complications is hindered and possibly a patient might not tolerate the absence of an immediately attending physician.

One possibility of solving this problem at least partially is to use magnetic resonance technology in the form of imaging in interventional procedures instead of X-ray procedures so that radiation exposure during an examination is eliminated.

Magnetic resonance imaging (subsequently referred to as MR imaging, MR standing for magnetic-resonance) is a field in medical imaging that has been successfully established since many years. Very simply stated, by using different magnetic fields of various strengths and spatial and timed characteristics, magnetic resonances are caused in an object to be examined. For this purpose, RF pulses with precisely defined frequencies are radiated by means of RF antennas. The magnetic resonances, on their part, are also being measured with RF antennas. More recently, MR imaging has been used also in the form of imaging during interventional procedures.

The interventional instruments used for such purposes have to be designed so as to be compatible with MR technology. This means that the use of instruments in the environment of MR equipment should not result in significant interferences with MR equipment (for instance, by disturbing sensitively adjusted magnetic fields) or endanger the patient.

For instance, from U.S. Pat. No. 6,701,176, a catheter is known which has at its head an RF antenna for MR imaging and also diagnostic electrodes to receive electric potentials. In addition, the head can have a tip for ablation of tissue. The head of the catheter is flexible and can be bent over control wires. Since the wires leading to the head of such a catheter are designed as electric conductors, there is the danger that the electric conductors are interacting with the RF energy of the MR equipment, which can result in problems. In order for the MR equipment not to be influenced by the HF energy of the ablation system and in order for the ablation system not to be influenced by the RF pulses of the MR equipment, filtering systems are disclosed in order to reduce undesirable HF or RF energy that might have been received.

It is also intended to design catheters in a simple and space-saving manner in order to use them in magnetic-resonant-supported interventional procedures.

SUMMARY OF THE INVENTION

It is an object of the invention to provide a space-saving catheter which can be used securely in magnetic-resonant-supported interventional procedures.

According to the invention, this objective is achieved by a catheter to be used in magnetic resonance-supported interventional procedures that has an electric cable which connects a first electric component attached to one catheter end with a second electric component attached t the other catheter end, at which the electric cable is coiled at least in sections.

By means of the coiled design of the electric cable, the inductance of the electric cable can be increased in a simple and space-saving manner. As a result, high inductance can be achieved even in comparatively thin catheters used to examine vascular systems. Consequently, if an RF current in the electric cable is induced by means of an RF pulse of the MR equipment, the RF current is absorbed to such an extent that neither the image quality of the MR imagining is significantly impaired nor is the patient endangered because of increasing heat in the electric cable.

Depending on the intended use, the first electric component that is attached to the catheter end which is to be inserted into a patient can be designed in different ways. For instance, the first electric component can be an RF transmitting or RF receiving antenna used for MR imaging. However, it can also be an HF antenna which is designed for irradiation of HF energy into the tissue for the purpose of coagulating the tissue. The first electric component can also be designed as an electro-optical transducer (for instance, a laser beam), or an electro-acoustic transducer (for instance, an ultrasound transducer) so that an ablation of tissue can be performed by laser energy or by ultrasound energy.

Depending on the embodiment of the first electric component, the second electric component can be adapted to the first one. For instance, the second electric component can supply electric or electromagnetic energy if the first electric component is used as an RF transmitting antenna, as HF antenna for the purpose of ablation of tissue, or as electro-optical or electro-acoustical transducer. The second electric component includes an output to tap electric or electromagnetic signals and transmit the signals to a processing unit of the MR equipment if the first electric component is designed as RF receiving antenna for MR imaging.

Preferably, a mechanism for bending one of the catheter ends is fed into the catheter.

In catheters used in X-ray radioscopic procedures, the tip can be designed magnetically to make it possible to navigate by means of external magnetic fields. This design is prohibited in magnetic resonance-supported interventional procedures. By the mechanism for bending one catheter end, it is possible to design a catheter in such a way that it can be led through a vascular system in as simple and reliable manner by bending the catheter end inserted into the body in various directions. Particularly if a catheter is designed with a component for the purpose of ablation of tissue, it can be led reliably to the place of ablation of tissue.

Preferably, the mechanism for bending one catheter end in the coiled sections of the electric cable passes at least partially through the coil. In this way, an especially space-saving and inexpensive arrangement of the electric cable and the mechanism that bends one catheter end can be achieved. In particular, it is possible in this way to provide the coils of the electric cable with the greatest possible cross-sectional surface so that inductivity is as high as possible.

Advantageously, in an end area of the catheter, the mechanism for bending one catheter end is fed in at the edge area of the catheter, and the electric cable proceeds inside the mechanism for bending. The arrangement of the mechanism for bending one catheter end at the edge area allows for a favorable power transmission for the purpose of bending one catheter end. Feeding the electric cable inside the mechanism for bending one catheter end achieves a space-saving arrangement even at the end area.

Preferably, the electric cable is designed as a coaxial cable.

In this case, in an embodiment, the sections of the electric cable that are coiled are at least partially formed as coaxial cable and are made in the form of a sheath wave trap. This can be easily achieved, for instance, by connecting in parallel a capacity to the outer shielding of the coaxial cable so that the resonant circuit thus created (with respectively matched inductance and capacities) effectively absorbs or eliminates HF waves induced at the outer shielding.

In an embodiment, the mechanism for bending one catheter end is designed as fluid lines formed in the end area of the catheter as a so-called "fluid muscle." By means of a pressure increase in the fluid lines or fluid muscles, compression of the fluid muscles is achieved, which results in contraction and bending of the respective catheter end.

Preferably, the fluid lines contain biocompatible fluid, for instance, sterile physiological saline. In this way, the patient will not be endangered by the fluid should it escape the fluid line.

In another embodiment, the mechanism for bending one catheter end is designed as Bowden cables. The retractable lines of the Bowden cables are flexible but mostly not expandable and consist of MR compatible material. To this end, it is possible to use, for instance, aramid fiber (known by the brand name Kevlar®), fiber glass cords, or carbon fiber cords.

In an advantageous embodiment, the first electric component of the catheter is designed as an RF antenna. Such RF antennas require supply or discharge cables designed mainly as coaxial cables so that the inventive embodiment of the catheter is especially advantageous.

BRIEF DESCRIPTION OF THE DRAWINGS

FIG. 4 shows a further embodiment of the inventive catheter.

DESCRIPTION OF THE PREFERRED EMBODIMENTS

Figure 1:
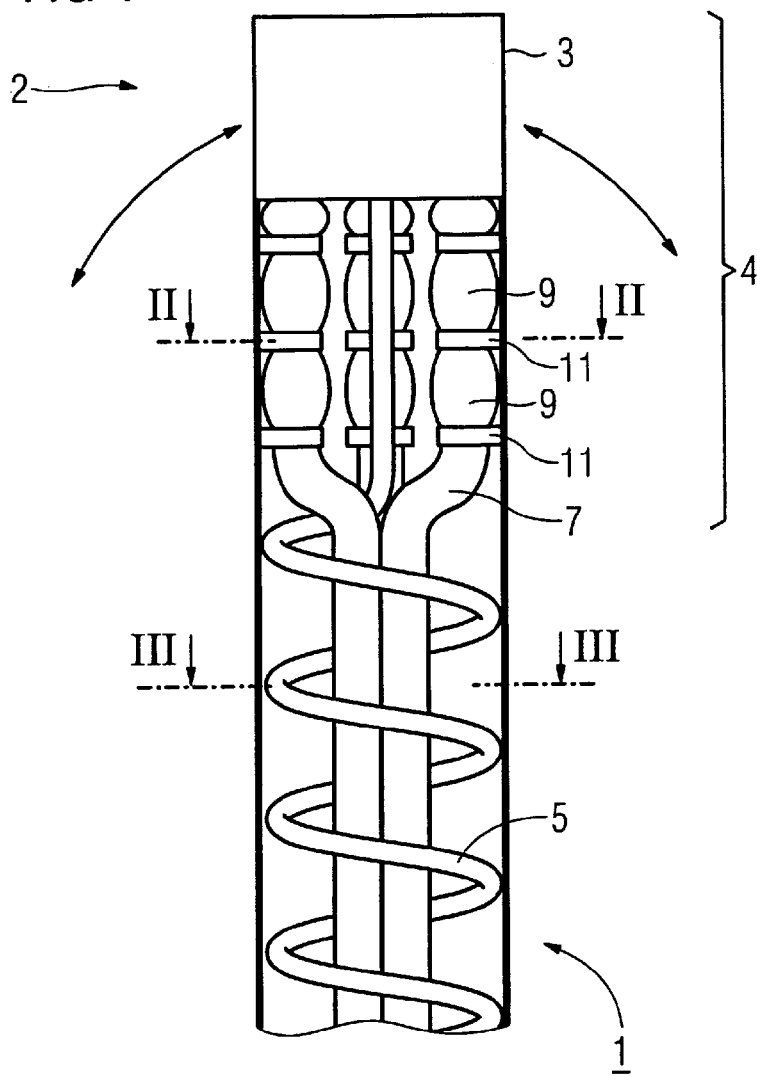
FIG. 1 shows an assembly of an embodiment of the inventive catheter.

FIG. 1 shows the assembly of a catheter 1, depicting the catheter end 1 to, be inserted. Depending on the use of the catheter 1, a differently designed first electric component 3 is arranged at this catheter end 2. For instance, the first electric component 3 can be designed as an HF antenna in order to feed HF energy into the tissue for the purpose of coagulating tissue. The first electric component 3 can also be designed as ultrasound probe or as laser source in order to allow for an ablation of tissue. In addition, it is possible to design the first electric component 3 as an RF transmitting or RF receiving antenna that can be used together with MR equipment for the purpose of irradiating RF pulses or receive magnetic resonance signals.

In all cases, for the purpose of controlling the first electric component, it is connected to an appropriately designed second component by means of an electric cable 5 (here designed in the form of coaxial cable).

If, for instance, the first electric component 3 is used as HF antenna for ablation of tissue, the second electric component provides HF energy and supplies it via the electric cable 5. If the first electric component 3 is used as an RF transmitting or receiving antenna for MR imaging, the second electric component is the connector to the MR equipment so that respective RF pulses can be remitted via this second component and via the electric cable 5, or received magnetic resonance signals can be supplies from the RF antenna to the processing units of the MR equipment. This also applies if the first electric component 3 is designed as ultrasound transducer or laser source.

One catheter end 2 can include further developments. Solely as an example, the one catheter end 2 can be designed for cryoablation (destruction of tissue by means of freezing), at which cooling agents are remitted to one catheter end 2 in an open or closed circuit. This circulatory system is also fed inside the coiled section of the electric cable 5.

Another possible variation of the embodiment allows for injection of a substance into the tissue via a needle. This can be used, for instance, to perform an alcoholic ablation (destruction of tissue by means of injections of alcohol). The supplying channels are also fed inside the coiled section of the electric cable 5.

Since the electric cable 5 is operated in the surroundings of MR equipment, there is the danger of the electric cable 5 interacting with RF fields used with the MR technology, which could result in various problems. For instance, the RF fields can increasingly heat the local electric cable 5 that this could endanger the patient. Furthermore, RF current induced in the electric cable 5 can interfere with the precisely coordinated magnetic fields used for MR imaging, resulting in impairment of the image quality.

According to the invention, the electric cable 5 is coiled inside the sheathing (jacketing) of the catheter 1. This increases inductance of the electric cable 5. If the electric cable 5 is designed as a coaxial cable, the coiling increases outer inductance. In this way, high inductance can be achieved to the extent that induced RF current is absorbed so much that neither the patient is endangered nor the image quality of the MR imagining is significantly impaired.

The catheter 1 is provided with a mechanism for bending one catheter end 2 of the two catheter ends in order to allow, for instance, for the possibility of being navigated through the vascular system of the patient. In the catheter 1 shown in FIG. 1, the mechanism for bending the catheter end 2 is designed as fluid lines 7 or, in the end area 4 of the catheter 1, as fluid muscles 9 which are connected to the sheathing of the catheter 1 by Bowden cables 11. To this end, the Bowden cables 11 are mounted at a distance of a few millimeters from each other. The fluid lines 7 or fluid muscles 9 at the end area of the catheter have an elastic design so that, as soon as the pressure in a fluid line 7 is increased, the fluid muscles 9 are balanced and contracted. This results in bending of one catheter end 2. In order to be able to bend the catheter 1 in various directions, at least three fluid lines 7 are required.

In the area of the catheter 1 in which the electric cable 5 is coiled, the fluid lines 7 are fed inside the coiling. In this way, an especially space-saving arrangement of the fluid lines and the electric cable can be achieved in the sheathing of the catheter 1, guaranteeing at the same time high inductivity of the electric cable. Only in the end area 4 of the catheter 1 in which the fluid muscles 9 are fed in at the edge area of the catheter sheathing 1, the electric cable 5 is guided centrally. However, even though the end area 4 is relatively short, i.e., at most a few centimeters long, with the electric cable 5 running in a straight line, the patient is not endangered and image quality is not significantly impaired.

Suitable fluids for the fluid line 7 are biocompatible gases and liquids, i.e., a fluid such as physiological saline which (should it escape the fluid line) would not be endanger the patient. This increases even more the safety of the patient because it would not endanger the patient even if the fluid line 7 was ruptured and fluid escaped into the body of the patient.

Figure 2:
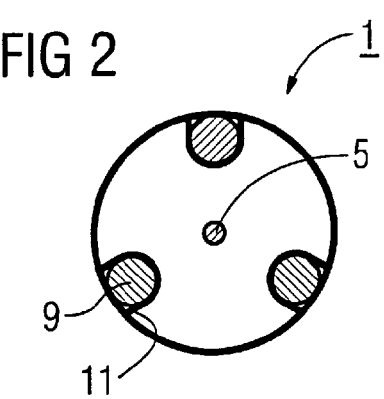
FIG. 2 and FIG. 3 respectively show different cross-sections through the catheter of FIG. 1.
Figure 3:
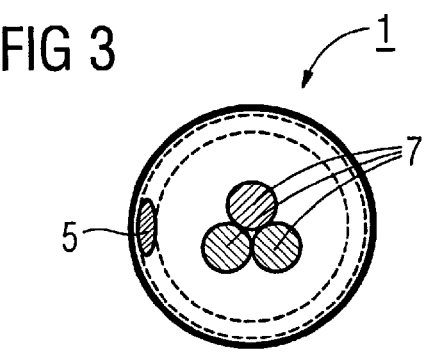

FIG. 2 and FIG. 3 each show a cross section of the catheter 1 according to FIG. 1 on the level of the dashed line II-II or III-III.

FIG. 2 clearly show the central electric cable 5 designed as coaxial cable and the fluid muscles 9 attached at the edge area of the catheter 1 via Bowden cables 11.

FIG. 3 shows at the edge area of the catheter 1 the coiled electric cable 5 designed as coaxial cable and the centrally guided fluid lines 7. The coiled electric cable 5 is fed in at the edge area of the catheter 1 and therefore the cross section of the coiling corresponds to the cross section of the catheter 1, achieving an increase of inductivity of the electric cable 5.

FIG. 4 shows a further embodiment of the invention-based catheter 1. The electric cable 5, which is also in this case designed as coaxial able, is coiled in some sections. In the coiled sections 13, capacitors 15 are attached to the outer shielding of the coaxial cable. Together with the inductance of the outer shielding of the coaxial cable, the capacitors 15 are adjusted to an operating frequency of the MR equipment in such a way that the sections 13 function as cable traps which are interconnected between the straight-running parts of the coaxial cable.

In contrast to the catheter depicted in FIG. 1, the mechanism for bending one catheter end 2 is designed as Bowden cables 17. Like the fluid lines 7, the Bowden cables 17 run in the coiled sections 13 inside the coil of the electric cable 5. Merely in the end areas 4 of the catheter 1, the Bowden cables 17 are fed to the edge area of the catheter 1 and attached there, so that one catheter end 2 is bent as soon as Bowden cable 17 is pulled.

The catheter 1 shown in FIG. 4 (indicated only schematically), depicts also the second electric component 19, which is arranged at the other end of the catheter, and control means 21 for the purpose of bending one catheter end 2.

In an embodiment of the catheter 1 several marker points 23 are arranged at one catheter end 2. The marker points 23 are designed in such a way that they are represented, clearly distinguishable, in a three-dimensional volume data set recorded by MR equipment. The geometrical arrangement of the marker points 23 makes it possible to make conclusions from an image of the catheter 1 as to the position and orientation of the catheter 1. This can be achieved, for instance, by three marker points 21 forming an irregular triangle on one level and a fourth marker point 21 is arranged outside of the level.

By determining the position and orientation of the catheter end 2, it is possible to support a user in operating the catheter 1, in particular in guiding the catheter 1 though a vascular system. For instance, intraluminal views of the vascular system can be produced from the sight of the catheter end 2, so that a physician is able to guide the catheter 1 through the vascular system from the sight of the catheter 1, similar to an optic endoscope being guided through the gastrointestinal tract.

Although modifications and changes may be suggested by those skilled in the art, it is the intention of the inventor to embody within the patent warranted hereon all changes and modifications as reasonably and properly come within the scope of his contribution to the art.

I claim as my invention:

1. A catheter for magnetic resonance-supported interventional procedures in an environment that subjects the catheter to radio-frequency pulses generated by a magnetic resonance imaging system, said catheter comprising a tubular catheter wall having an interior surface that defines an interior of said catheter in which an electric cable is connected that connects a first electric component mounted at a first catheter end with a second electric component mounted at a second catheter end, said electric cable being susceptible to having RF current therein due to interaction of said electric cable with said RF pulses, and said electric cable being coiled around a coil axis in at least one coiled section thereof with a coiling configured to produce an inductance that absorbs said RF current, said at least one coiled section having a coiled section exterior that is radially outwardly spaced from said coil axis and radially inwardly spaced from said interior surface and said catheter comprising a mechanism operable to bend at least one of said first and second catheter ends, said mechanism being selected from the group consisting of a Bowden cable and fluid lines forming a fluid muscle, and wherein a portion of said mechanism operable to bend one of said first and second catheter ends is located in a space between said coiled section exterior and said interior surface of said catheter.

2. A catheter according to claim 1, wherein the electric cable is a coaxial cable.

3. A catheter according to claim 2, wherein said at least one coiled section of the electric cable formed by the coaxial cable forms a sheath wave trap.

4. A catheter according to claim 1, wherein said mechanism is fluid lines forming a fluid muscle, and wherein the fluid lines contain a biocompatible liquid.

5. A catheter according to claim 1, wherein the first electrical component of the catheter is designed as an RF antenna.

6. A catheter according to claim 1 wherein said coiling is configured to produce an inductance that absorbs said RF current to an extent that precludes said RF current from interfering with generation of a magnetic resonance image.

* * * * *